(12) United States Patent
Navarro

(10) Patent No.: US 8,052,420 B2
(45) Date of Patent: Nov. 8, 2011

(54) APPARATUS AND METHOD FOR ADJUSTING ORTHODONTIC WIRE

(76) Inventor: Carlos F. Navarro, Dallas, TX (US)

(*) Notice: Subject to any disclaimer, the term of this patent is extended or adjusted under 35 U.S.C. 154(b) by 93 days.

(21) Appl. No.: 12/608,185

(22) Filed: Oct. 29, 2009

(65) Prior Publication Data

US 2011/0104629 A1   May 5, 2011

(51) Int. Cl.
*A61C 3/00* (2006.01)

(52) U.S. Cl. ............................. 433/4; 433/155

(58) Field of Classification Search .............. 433/4, 159; 81/303, 304, 306, 308, 310, 311, 312; D08/23, D08/52, 53, 54, 55, 56, 57, 58; D24/143, D24/152, 153

See application file for complete search history.

(56) References Cited

U.S. PATENT DOCUMENTS

| | | | | |
|---|---|---|---|---|
| 429,989 | A * | 6/1890 | Adams | 72/384 |
| 1,064,404 | A * | 6/1913 | Walker | 433/4 |
| 1,103,606 | A * | 7/1914 | Montag | 72/383 |
| 1,141,916 | A * | 6/1915 | Aderer | 72/390.5 |
| 1,299,103 | A * | 4/1919 | Angle | 433/4 |
| 1,304,720 | A | 5/1919 | Young | |
| 1,594,143 | A * | 7/1926 | Angle et al. | 433/4 |
| D90,137 | S * | 6/1933 | Gutsche | D32/35 |
| 2,755,692 | A * | 7/1956 | Wallshein | 72/390.5 |
| 2,828,780 | A * | 4/1958 | Gray | 140/123 |
| 2,954,606 | A * | 10/1960 | Peak | 433/4 |
| 2,959,858 | A * | 11/1960 | Drake | 433/4 |
| 3,244,201 | A * | 4/1966 | Wallshein | 140/106 |
| 3,774,306 | A * | 11/1973 | Dobyns | 433/4 |
| 3,918,472 | A * | 11/1975 | Brown | 140/106 |
| 4,040,186 | A * | 8/1977 | Kalvelage | 433/4 |
| 4,043,364 | A * | 8/1977 | Rose | 140/106 |
| 5,084,935 | A * | 2/1992 | Kalthoff | 7/132 |
| 5,168,616 | A * | 12/1992 | Klein | 29/268 |
| 5,197,880 | A * | 3/1993 | Lovaas | 433/159 |
| 6,327,945 | B1 * | 12/2001 | Perez Romo | 81/426 |
| 6,776,615 | B2 * | 8/2004 | Dietrich | 433/159 |
| 6,984,126 | B1 * | 1/2006 | Graham | 433/4 |
| D545,653 | S * | 7/2007 | Kirkpatrick | D8/52 |

OTHER PUBLICATIONS

PCT, Notification of Transmittal of the International Search Report and the Written Opinion of the International Searching Authority, or the Declaration, International Application No. PCT/US2010/053894, 10 Pages, Mailed Feb. 15, 2011.

* cited by examiner

*Primary Examiner* — Thomas J Sweet
*Assistant Examiner* — Christopher Sponheimer
(74) *Attorney, Agent, or Firm* — Baker Botts L.L.P.

(57) ABSTRACT

A handheld apparatus for adjusting orthodontic wire includes first and second handle portions and a jaw portion. The first handle portion pivotably couples to the second handle portion such that the first and second handle portions are capable of pivoting with respect to each other at a pivot axis. The jaw portion extends from the first and second handle portions. The jaw portion includes: a first prong extending from the first handle portion; and second and third prongs extending from the second handle portion. The second and third prongs each include: a respective inner surface that partially defines a slot between the second and third prongs; and first and second outer surfaces joined together by a transition region.

14 Claims, 6 Drawing Sheets

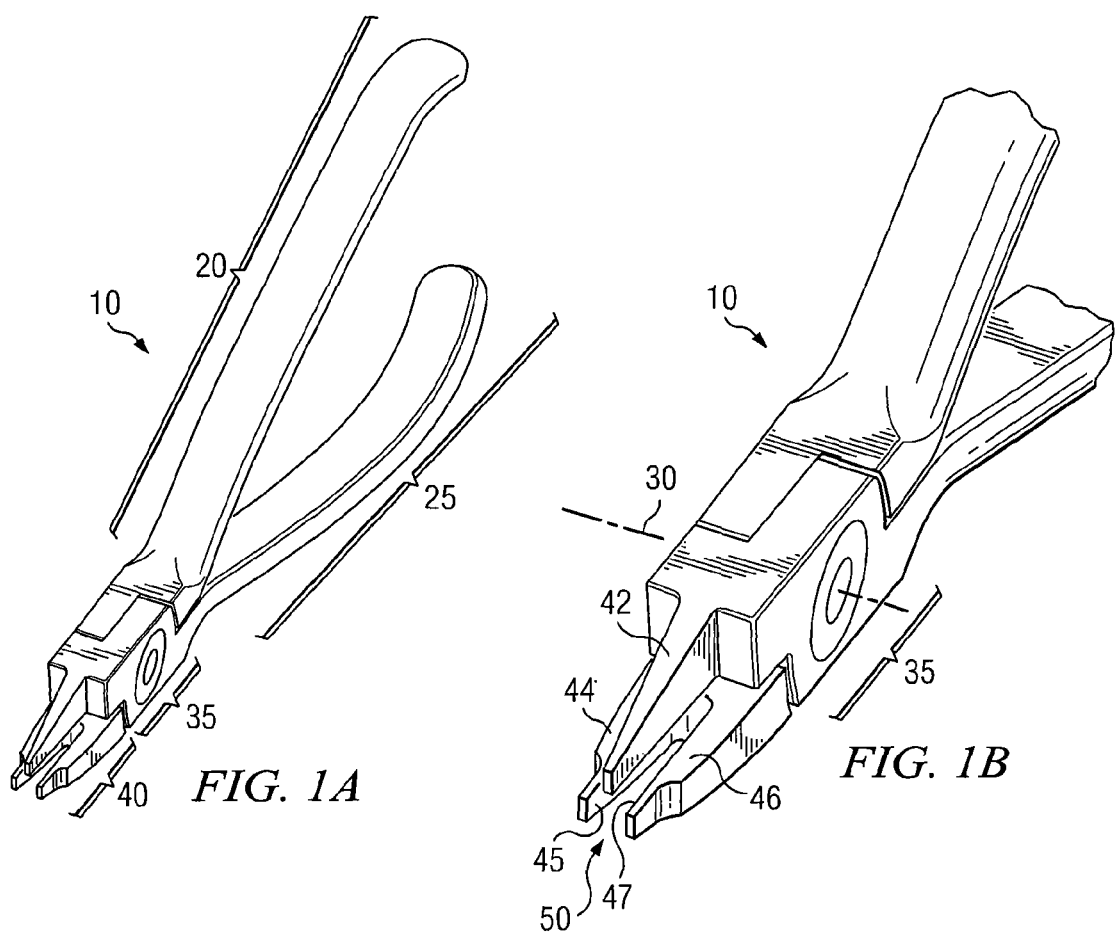
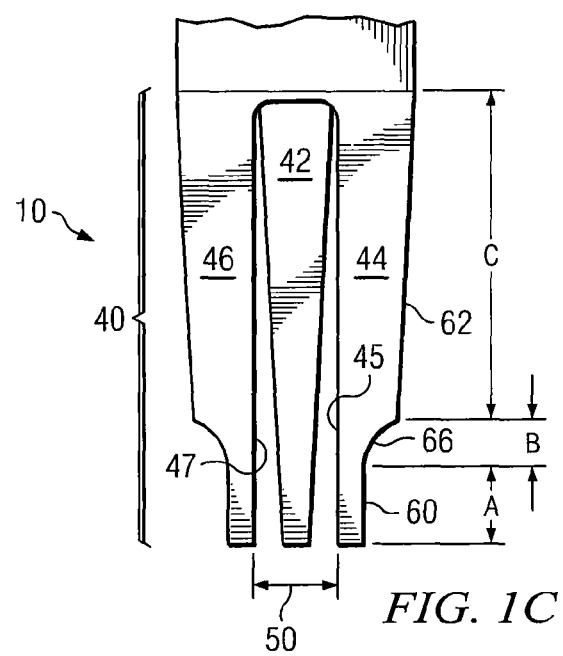

APPARATUS AND METHOD FOR ADJUSTING ORTHODONTIC WIRE

TECHNICAL FIELD

This invention relates generally to dentistry and orthodontics and in particular to an apparatus and method for adjusting orthodontic wire.

BACKGROUND

Arch wires are frequently used in orthodontic techniques to transmit correctional forces used to align the teeth. The forces applied by arch wires may be capable of moving a tooth in a particular direction over time. A resulting stress is created within the periodontal ligament. The modification of the periodontal blood supply determines a biological response which leads to bone remodeling, where bone is created on one side by osteoblast cells and resorbed on the other side by osteoclast cells. Arch wires may be adjusted at various locations to create particular moments of force.

SUMMARY OF THE INVENTION

The apparatus and method of the present invention may reduce or eliminate certain problems and disadvantages associated with previous dental and orthodontic apparatus and methods for adjusting orthodontic wire.

According to one embodiment, a handheld apparatus for adjusting orthodontic wire includes first and second handle portions and a jaw portion. The first handle portion pivotably couples to the second handle portion such that the first and second handle portions are capable of pivoting with respect to each other at a pivot axis. The jaw portion extends from the first and second handle portions. The jaw portion includes a first prong extending from the first handle portion. The jaw portion also includes second and third prongs extending from the second handle portion. The second and third prongs are separated from each other by a slot. The second and third prongs each include a respective inner surface that partially defines the slot. Each inner surface is disposed substantially along a plane substantially perpendicular to the pivot axis. In addition, the second and third prongs each include first and second outer surfaces joined together by a transition region. The first outer surface is closer than the second outer surface to the plane of the inner surface substantially perpendicular to the pivot axis. The second outer surface is closer than the first outer surface to the pivot axis. The first and second handle portions may be further configured to pivot with respect to each other at the pivot axis such that the first prong opposes the slot separating the second and third prongs. In particular embodiments, the maximum distance between the first outer surfaces of the second and third prongs along a line parallel to the pivot axis may be less than or equal to 6 mm; and the minimum distance between the second outer surfaces of the second and third prongs along a line parallel to the pivot axis may be greater than or equal to 4 mm.

Particular embodiments may provide one or more technical advantages. In various embodiments, multi-pronged pliers may enable intra-oral adjustments to an arch wire while the arch wire is coupled to a patient's teeth. Some adjustments to an arch wire may be made at locations in proximity to various obstructions. For example, some embodiments may facilitate manipulation of prong tips between orthodontic brackets and/or between an arch wire and the patient's teeth. Various embodiments may be enable arch wire adjustments at locations that provide very little workable space, such as, for example, between brackets on adjacent teeth of a pediatric patient.

In addition, some embodiments may be configured in a manner that enables manipulation of the prong tips within confined spaces while mitigating the risk of deforming the prong tips or damaging the arch wire during an adjustment. For example, some or all of the prongs may be shaped to include a thinner tip-region that is joined to a thicker base-region by a transition region. Example transition regions that may be used to join a prong tip to the base of the prong may include a fillet, a step, a tapered step, an S-curve, etc. In particular embodiments, the thinner tip-region, the thicker base-region, and the transition region may be configured to establish a suitable balance between manipulability of the prong within confined spaces and structural rigidity of the prong. Such configurations may be contrasted with conventional prongs that are linearly tapered from tip to base and that have no transition regions between prong tips and bases.

Certain embodiments may provide all, some, or none of these advantages. Certain embodiments may provide one or more other advantages, one or more of which may be apparent to those skilled in the art from the figures, descriptions, and claims included herein.

BRIEF DESCRIPTION OF THE DRAWINGS

For a more complete understanding of the present invention and advantages thereof, reference is now made to the following description taken in conjunction with the accompanying drawings, in which:

FIGS. 1A, 1B and 1C illustrate multiple views of a handheld apparatus for adjusting dental and orthodontic wire according to one embodiment;

DESCRIPTION OF EXAMPLE EMBODIMENTS

Figure 1D:
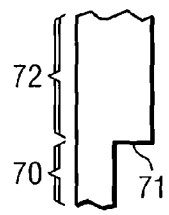
FIGS. 1D, 1E, and 1F illustrate alternative prong shapes for a handheld apparatus for adjusting dental and orthodontic wire according to various embodiments.

The apparatus and method of the present invention may reduce or eliminate certain problems and disadvantages associated with previous dental and orthodontic apparatus and methods for adjusting orthodontic wire. For example, conventional wire adjustments typically involve time-consuming procedures and rely on the clinician's skills. In addition, the adjustment of arch wires conventionally involves removing an arch wire from the patient's mouth and subsequently reinstalling the arch wire after making extra-oral adjustments to the wire.

In various embodiments, multi-pronged pliers may enable intra-oral adjustments to an arch wire while the arch wire is coupled to a patient's teeth. Some adjustments to an arch wire may be made at locations in proximity to various obstructions. For example, some embodiments may facilitate manipulation of prong tips between orthodontic brackets and/or between an arch wire and the patient's teeth. Various embodiments may be enable arch wire adjustments at locations that provide very little workable space, such as, for example, between brackets on adjacent teeth of a pediatric patient. Certain wire adjustments may be performed with relative ease and without requiring particularized clinician skill, thereby potentially saving time and cost.

In addition, some embodiments may be configured in a manner that enables manipulation of the prong tips within confined spaces while mitigating the risk of deforming the prong tips or damaging the arch wire during an adjustment. For example, some or all of the prongs may be shaped to include a thinner tip-region that is joined to a thicker base-region by a transition region. Example transition regions that may be used to join a prong tip to the base of the prong may include a fillet, a step, a tapered step, an S-curve, etc. In particular embodiments, the thinner tip-region, the thicker base-region, and the transition region may be configured to establish a suitable balance between manipulability of the prong within confined spaces and structural rigidity of the prong. Such configurations may be contrasted with prongs that are linearly tapered from tip to base and that have no transition regions between prong tips and bases.

Particular embodiments disclosed herein are capable of bending arch wires employing a shape memory alloy. For example, certain embodiments disclosed herein may be capable of making "first order" bends (e.g., inward and/or outward) or "second order" bends (upward and/or downward) in the arch wire using a beveled jaw having a single prong portion and a double prong portion. In certain embodiments, the closing action of the pliers produces wire bends ranging from approximately 25 to 30 degrees. Various embodiments may be particularly helpful in crucial stages of treatment, such as leveling. For example, multiple and precise second order bending of an orthodontic wire can be performed to exert an extrusion force or forces on orthodontic brackets attached to the teeth. In certain embodiments, the bending may include forming an exaggerated curve of Spee in the maxillary arch wire and a reverse curve of Spee in the mandibular arch wire.

Particular examples and dimensions specified throughout this document are intended for example purposes only, and are not intended to limit the scope of the present disclosure. Moreover, the illustrations in FIGS. 1A through 5 are not necessarily drawn to scale.

FIGS. 1A, 1B and 1C illustrate multiple views of a handheld apparatus 10 for adjusting dental and orthodontic wire according to one embodiment. Handheld apparatus 10 may be used to make bends in an orthodontic arch wire, which, in turn, adjust the corrective forces applied to a patient's teeth. For example, handheld apparatus 10 may be used to adjust to adjust an orthodontic arch wire to correct crowding, misalignment, etc. of a patient's teeth. As described further below, particular embodiments may be used to make intra-oral adjustments to an arch wire while the arch wire is coupled to a patient's teeth.

As illustrated in FIG. 1A, handheld apparatus 10 is a pair of pliers that includes a first handle portion 20 pivotably coupled to a second handle portion 25. The first and second handle portions 20 and 25 are capable of pivoting with respect to each other at a pivot axis 30. The pivoting of handle portions 20 and 25 is transmitted to a jaw portion 40 via a linkage arrangement 35. For example, movement of the handle portions 20 and 25 toward each other may enable a closing action of jaw portion 40. Conversely, movement of handle portions 20 and 25 away from each other may enable an opening action of jaw portion 40. In the illustrated embodiment, handle portions 20 and 25 are ergonomically shaped; however, handle portions 20 and 25 may have any suitable shape to be gripped and manipulated by hand.

Referring to FIGS. 1B and 1C, jaw portion 40 includes three prongs 42, 44, and 46. In this example, the prongs 42, 44, and 46 of jaw 40 are configured such that a plane can be drawn that is parallel and through pivot axis 30, that evenly divides the space between handle portions 20 and 25, and that divides the space between prong 42 and each of prongs 44 and 46. Prong 42 extends from handle portion 25. Prongs 44 and 46 extend from handle portion 20. In particular embodiments, prong 42 and handle portion 25 may be formed from a single piece of metal; and prongs 44 and 46 and handle portion 25 may also be formed from a single piece of metal. For example, prong 42 and handle portion 20 may be forged and/or milled from a single piece of stainless steel; and prongs 44 and 46 and handle portion 25 may be forged and/or milled from another single piece of stainless steel. In particular embodiments, a single-piece construction of prongs 44 and 46 and handle portion 25 may mitigate flaring of prongs 44 and 46 and enhance the strength of their coupling to handle portion 25. Although the jaw portion of the illustrated embodiment includes three prongs 42, 44, and 46, in alternative embodiments, any suitable number of prongs may be used. In addition, although prongs 42, 44, and 46 and handle portions 20 and 25 are forged and/or milled from respective pieces of metal, in alternative embodiments, handheld apparatus may be formed from a number of metallic and/or non-metallic material(s) using any suitable manufacturing technique(s).

In this example, prongs 44 and 46 are at least partially separated from each other by a slot 50. The shape of slot 50 is defined in part by inner surfaces 45 and 47 of prongs 44 and 46, respectively. Inner surfaces 45 and 47 are disposed along respective planes that are substantially parallel to each other and perpendicular to rotation axis 30. Although inner surfaces 45 and 47 are shown as substantially parallel to each other in this example, in alternative embodiments inner surfaces 45 and 47 may be slightly angled relative to a plane perpendicular to pivot axis 30. For example, surfaces 45 and 47 may be disposed along respective planes at angles within the range of approximately 1 to 5 degrees (e.g., 3 degrees) relative to a plane perpendicular to pivot axis 30.

Prongs 44 and 46 have respective outer surfaces (e.g., outer surfaces 60-62 of prong 44 illustrated in FIG. 1C) that are disposed opposite from inner surfaces 45 and 47, respectively, and that are substantially symmetric to each other relative to a plane perpendicular to rotation axis 30. Prong 42 is positioned relative to prongs 44 and 46 such that prong 42 opposes substantially all of slot 50 as jaw portion 40 approaches a closed position. Although prong 42 opposes substantially all of slot 50 as jaw portion 40 approaches a closed position, in alternative embodiments, prongs 42, 44, and 46 and slot 50 of jaw portion 40 may have alternative configurations.

In particular embodiments, prongs 42, 44, and 46 may be configured in a manner that enables their manipulation at locations in proximity to various obstructions. For example, some embodiments may facilitate manipulation of prong tips between orthodontic brackets and/or between an arch wire and the patient's teeth. Various embodiments may be enable arch wire adjustments at locations that provide very little workable space, such as, for example, between brackets on adjacent teeth of a pediatric patient.

In addition, some embodiments may be configured in a manner that enables manipulation of the prong tips within confined spaces while mitigating the risk of deforming the prong tips or damaging the arch wire during an adjustment. For example, the wire contact surfaces of prongs 42, 44, and/or 46 may include one or more chamfered or rounded edges that may mitigate damaging an arch wire during an adjustment. As another example, prongs 42, 44, and/or 46 may be shaped to include a thinner tip-region that is joined to a thicker base-region by a transition region. In particular embodiments, the thinner tip-region, the thicker base-region, and the transition region of a prong may be configured to establish a suitable balance between manipulability of the prong within confined spaces and structural rigidity of the prong. Such configurations may be contrasted with conventional prongs that are linearly tapered from tip to base and that have no substantial transition region(s) between the tip and base of the prong. If these conventional prongs are too thick, they may not be readily manipulated between obstructions, such as, for example, between narrowly spaced orthodontic brackets, including brackets installed in pediatric patients. Some prongs may have thicknesses that prohibit any manipulation that would enable wire adjustments between narrowly spaced obstructions. Conversely, if these conventional prongs are too thin, their tips may deform during an adjustment of an arch wire as force is applied to the tips. Embodiments with particular transition regions joining more maneuverable prong tips to a sturdier prong base, however, may optimize the balance of structural rigidity and prong-tip maneuverability in proximity to or between obstructions, such as, for example, between narrowly spaced orthodontic brackets, including brackets installed in pediatric patients.

Referring to FIG. 1C, for example, prongs 44 and 46 may each include a thinner tip-region that is joined to a thicker base-region by a transition region. Outer surfaces 60, 62, and 66 at least partially define a thinner tip-region A, a transition region B, and a thicker base-region C, respectively, for prong 44. In the illustrated embodiment, surfaces 60, 62, and 66 of prong 44 are not coplanar to each other and the maximum distance between surface 60 and inner surface 45 is less than the maximum distance between surface 62 and inner surface 45. In a particular embodiment, for example, the maximum distance between surface 60 and inner surface 45 may be within the range of approximately 0.5 mm to 1.5 mm (e.g., 1 mm); and the maximum distance between surface 62 and inner surface 45 may be within the range of approximately 2 mm to 3 mm (e.g., 2.5 mm). In this example, thinner tip-region A has a length, disposed along surface 60 in a direction toward the pivot axis 30, within the range of approximately 2 mm to 4 mm (e.g., 3 mm); and thicker tip-region C has a length, disposed along surface 62 in a direction toward the pivot axis 30, within the range of approximately 1 cm to 2 cm (e.g., 1.4 cm). In addition, surface 62 is closer to the pivot axis 30 than surface 60 in this example. Although thinner tip-region A of prong 44 has a substantially rectangular cross-section in this example, the thinner tip-region A may have any suitable cross-section including, for example, a cross-section that is square, circular, elliptical, diamond, a cross-section that is shaped in part by one or more chamfered edges or angled corners, etc.

In the illustrated embodiment, transition region C of prong 44, generally indicated by surface 66, is a rounded fillet disposed between and connected to each of surfaces 60 and 62. The fillet has a radius substantially equal to the distance between planes that substantially define surfaces 60 and 62 at respective locations where surfaces 60 and 62 join surface 66; however, any suitable dimensions may be used. In particular embodiments, the fillet joining surface 60 to surface 62 may contribute to the structural rigidity of prong 44 by maximizing the forces that are distributed away from the tip of prong 44. In addition, the fillet may be configured to assist in manipulating prong 44 around various obstructions.

Figure 1E:
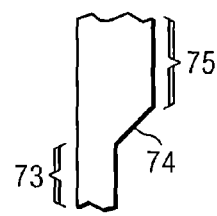
Figure 1F:
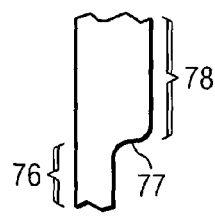

Although a fillet is used to join surfaces 60 and 62 in the illustrated embodiment, any suitable transition joining surface 60 to surface 62 may be used that enables manipulation of prongs 42, 44, and 46 at locations in proximity to various obstructions while at the same time mitigating the risk of deforming the prong tips or damaging the arch wire during an adjustment. For example, the transition(s) in alternative embodiments may include one or more steps, tapered steps, S-curves, etc. FIGS. 1D, 1E, and 1F illustrate a step transition, a tapered-step transition, and an S-curve transition, respectively, according to various embodiments. As shown in FIG. 1D, a transition region 71 is joined to a thinner tip-region 70 and a thicker base-region 72 at substantially ninety degree angles. As shown in FIG. 1E, however, a transition region 74 and a thinner tip-region 73 are joined together at an angle greater than 90 degrees. Although FIG. 1E illustrates angular corners joining transition region 74 to thinner tip-region 73 and a thicker base-region 75, in alternative embodiments the boundaries joining these regions may be rounded. As shown in FIG. 1F, a transition region 77 joins a thinner tip-region 76 to a thicker base-region 78 in a manner substantially defined by an S-curve. Thus, a variety of transition regions may be used to maximize the structural rigidity of a prong while at the same time enabling the tip of the prong to be thinned for particular applications.

In operation, handheld apparatus 10 may be used to make one or more adjustments to an orthodontic arch wire. For example, a user may grip handle portions 20 and 25 in a manner that transmits forces to an arch wire via jaw portion 40. In various embodiments, prongs 42, 44, and/or 46 may be configured in a manner that may enable intra-oral adjustments to an arch wire while the arch wire is coupled to a patient's teeth. Some adjustments to an arch wire may be made at locations in proximity to various obstructions. For example, some embodiments may facilitate manipulation of prongs 42, 44, and 46 between orthodontic brackets and/or between an arch wire and the patient's teeth, as described further below.

Figure 2A:
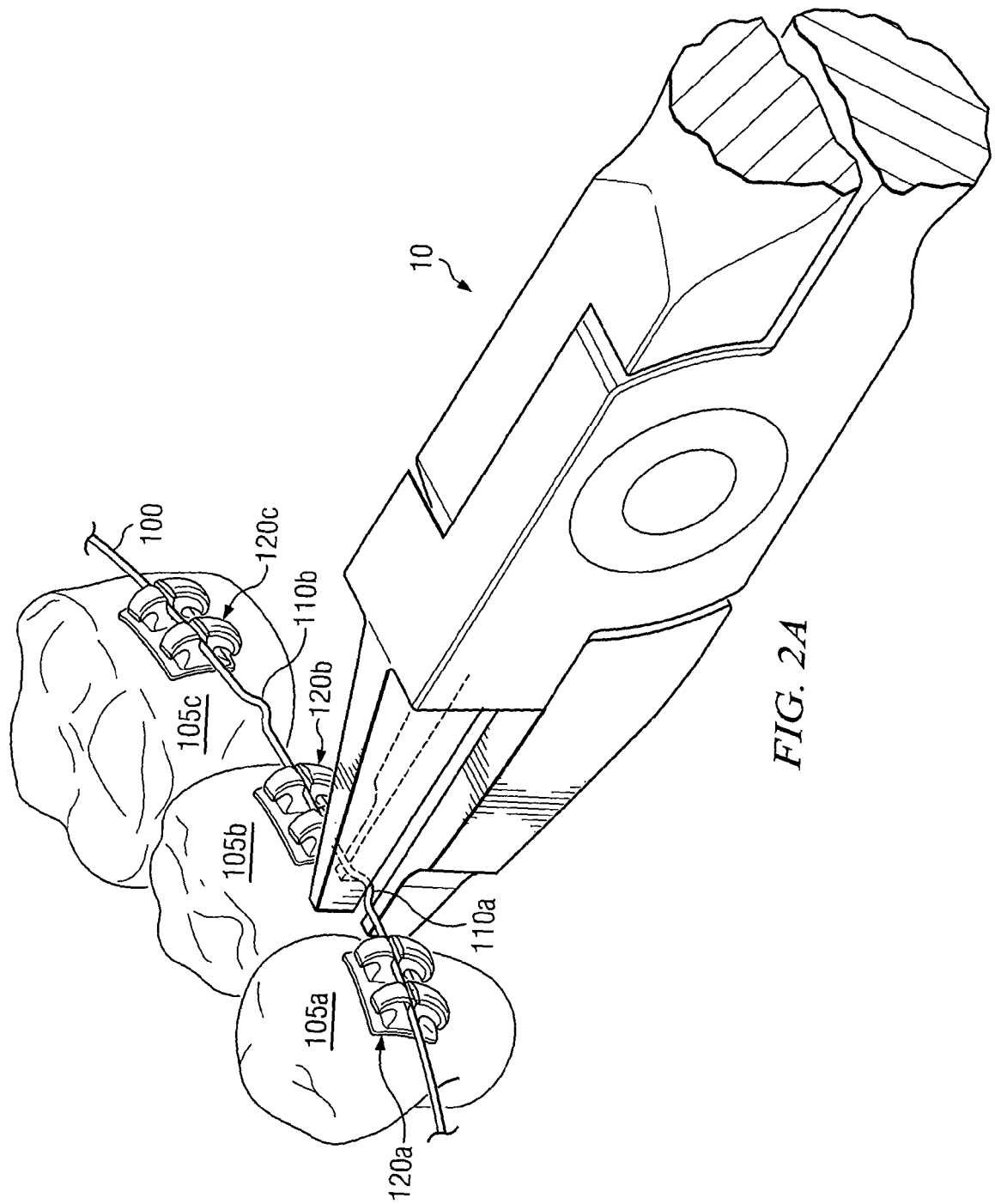
FIGS. 2A and 2B illustrate example wire adjustments that may be made using the handheld apparatus illustrated in FIGS. 1A through 1C according to one embodiment.
Figure 2B:
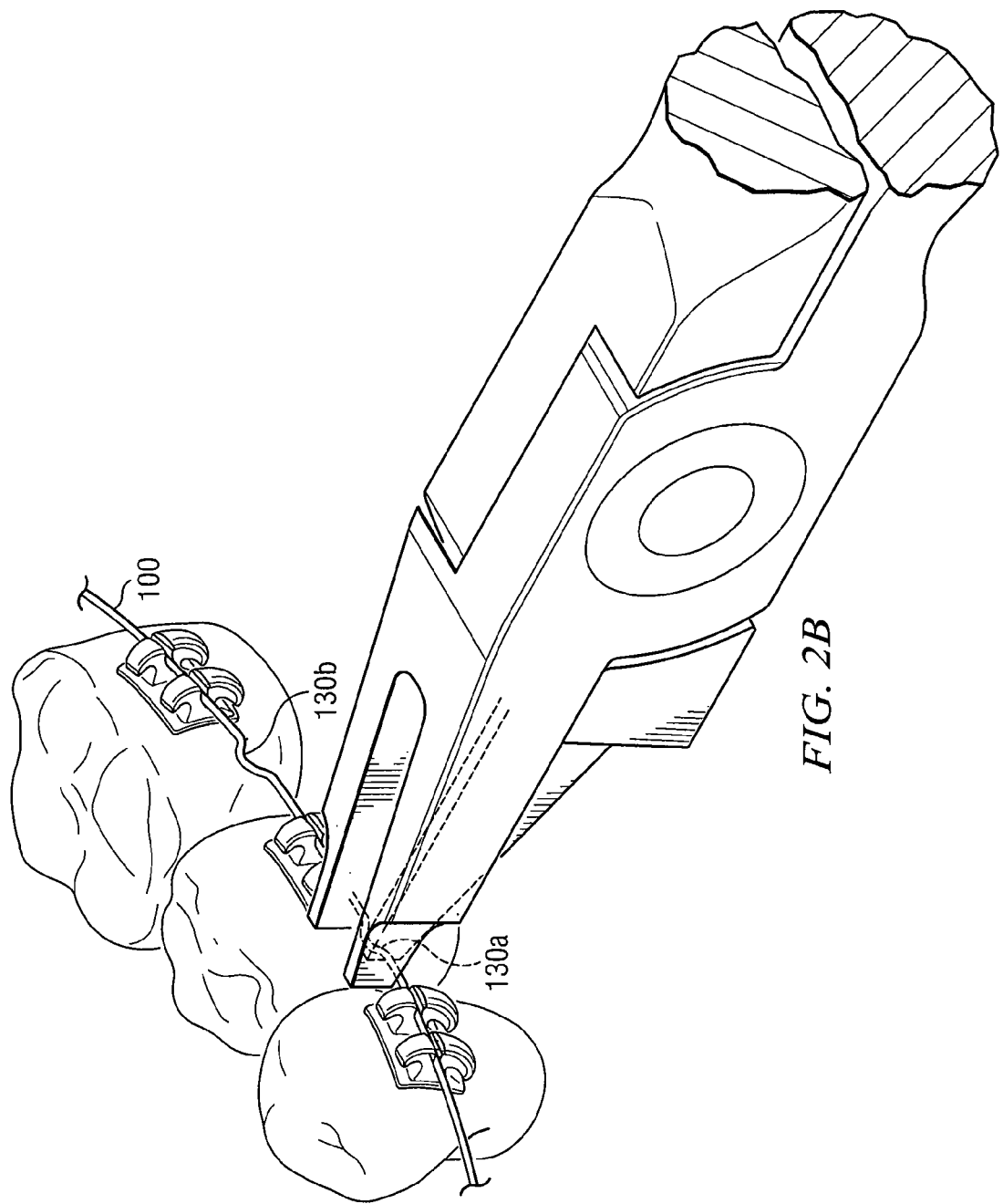

FIGS. 2A and 2B illustrate example adjustments that may be made to an orthodontic arch wire 100 using handheld apparatus 10. The illustrated examples of FIGS. 2A and 2B show "second order" (upward and/or downward) intra-oral bending of an orthodontic arch wire 100 coupled to a patient's teeth 105*a*, 105*b*, and 105*c*. As shown in FIG. 2A, handheld apparatus 10 may be manipulated so as to form downward-directional bends 110*a* and 110*b* in arch wire 100. Bends 110*a* and 110*b* have contours that are controlled at least in part by the shape and spacing of prongs 42, 44, and 46 and the force applied to wire 110 via jaw portion 40 of handheld apparatus 10.

In this example, prongs 42, 44, and 46 are shaped in a manner that enables their manipulation in proximity to or between obstructions, such as, for example, between orthodontic brackets 120*a* and 120*b* and/or between brackets 120*b* and 120*c*. Thus, particular embodiments of handheld apparatus 10 may be used to make controlled adjustments of arch wire 100 at a location between two closely spaced brackets that, in some cases, may be coupled to adjacent teeth 105*a*, 105*b*, and/or 105*c*.

In the alternative example shown in FIG. 2B, handheld apparatus 10 may be inverted so as to enable the formation of upward-directional bends 130*a* and 130*b* in arch wire 100. Although FIGS. 2A and 2B illustrate example intra-oral bending of an orthodontic arch wire 100 while arch wire 100 is coupled to a patient's teeth 105*a*, 105*b*, and 105*c*, handheld apparatus 10 may also be used to bend wires outside of a patient's mouth and may be used to make a variety of alternative types of wire adjustments.

Figure 3:
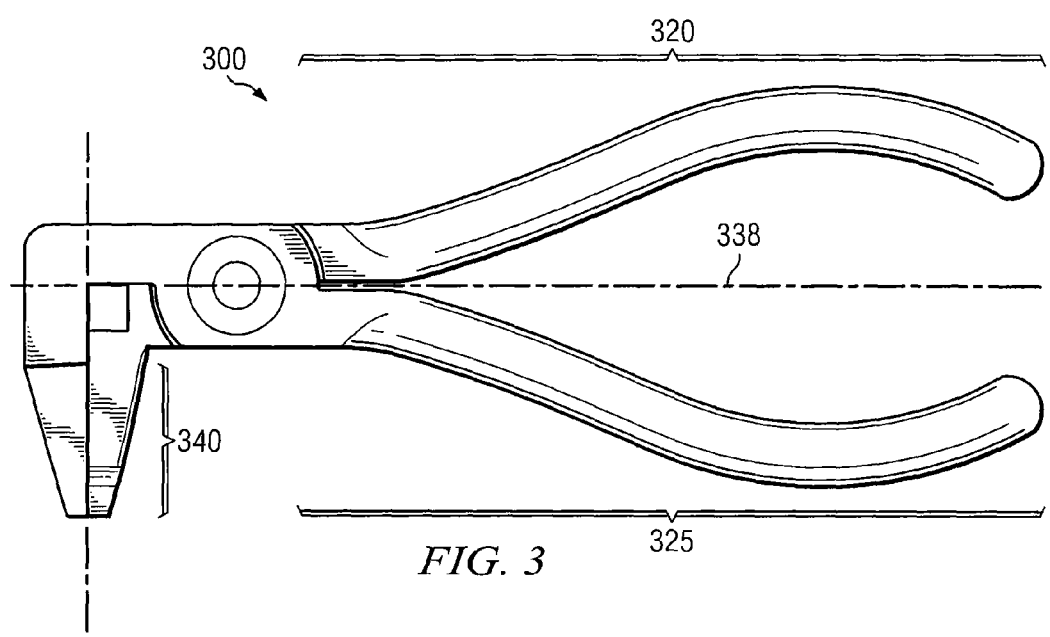
FIG. 3 illustrates a lateral view of a handheld apparatus for adjusting dental and orthodontic wire according to one embodiment.

FIG. 3 illustrates a lateral view of a handheld apparatus 300 for adjusting dental and orthodontic wire according to another embodiment. In this example, handheld apparatus 300 is substantially similar in structure to handheld apparatus 10, with the exception that a three-prong jaw portion 340 of handheld apparatus 300 extends laterally from a pair of handle portions 320 and 325 at approximately a ninety degree angle relative to a plane 338 that extends through and bisects apparatus 300 such that plane 338 is equidistant from handle portions 320 and 325 and evenly divides the space between handle portions 320 and 325. In this example, plane 338 is parallel and through the pivot axis.

Figure 4:
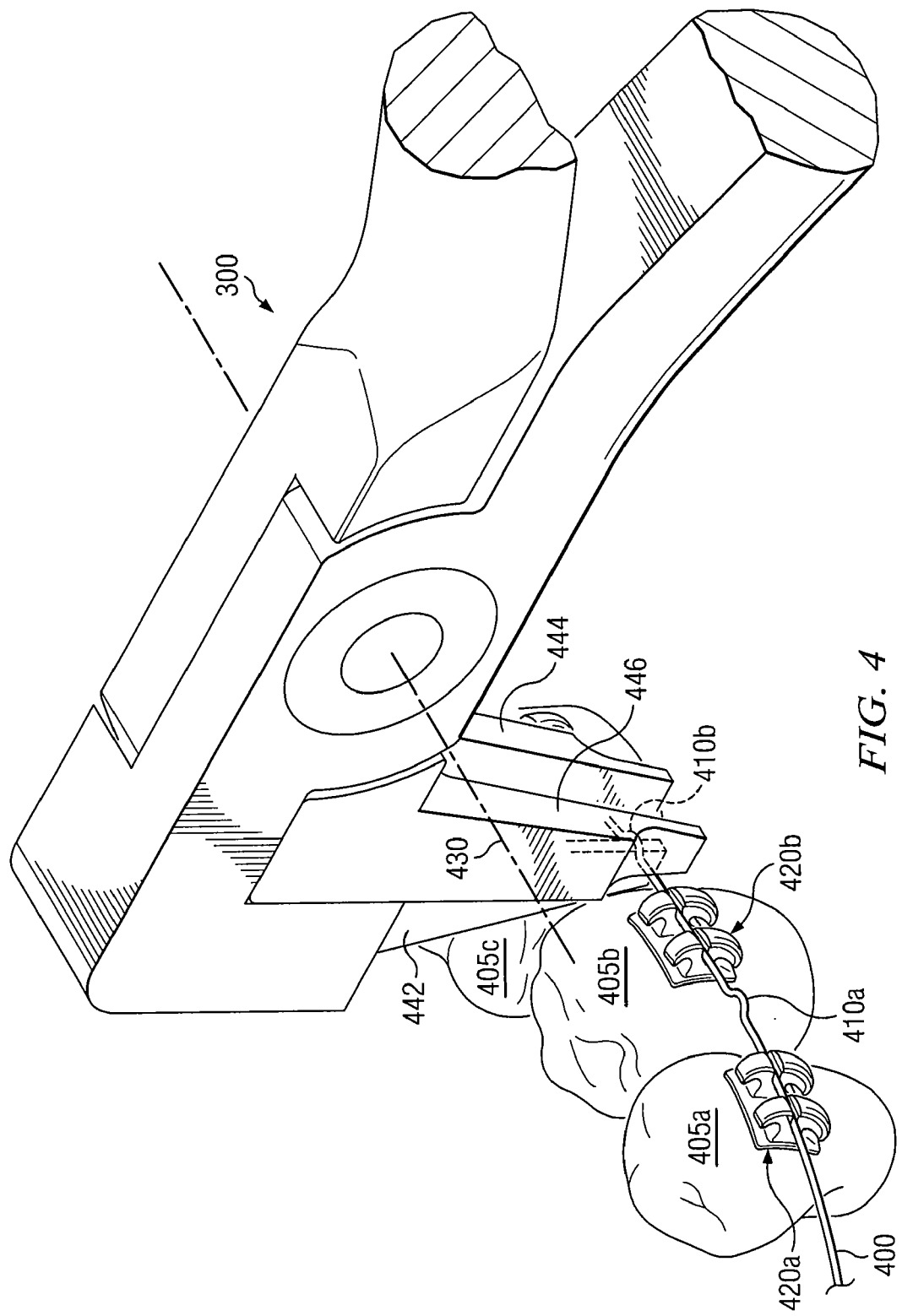
FIG. 4 illustrates example wire adjustments that may be made to an orthodontic arch wire using the handheld apparatus illustrated in FIG. 3.

FIG. 4 illustrates example adjustments that may be made to an orthodontic arch wire 400 using handheld apparatus 300. As shown in FIG. 4, handheld apparatus 300 may be manipulated so as to form outward-directional bends 410a and 410b in an orthodontic arch wire 400. The three prongs 442, 444 and 446 of handheld apparatus 400 may be shaped in a manner that enables their manipulation between brackets 420. Thus, particular embodiments of handheld apparatus 400 may be used to make controlled "first order" (inward and/or outward) intra-oral adjustments of orthodontic arch wire 400 at a location between two closely spaced brackets 420a and 420b coupled to teeth 405a and 405b, respectively. Handheld apparatus 400 may also be used to bend arch wires outside of a patient's mouth and may be used to make a variety of alternative bends oriented in alternative directions. In this example, prong 442 is further from a pivot axis 430 of handheld apparatus 300 than prongs 444 and 446. However, in alternative embodiments prong 442 may be closer to pivot axis 430 than prongs 444 and 446, as described further with reference to FIG. 5.

Figure 5:
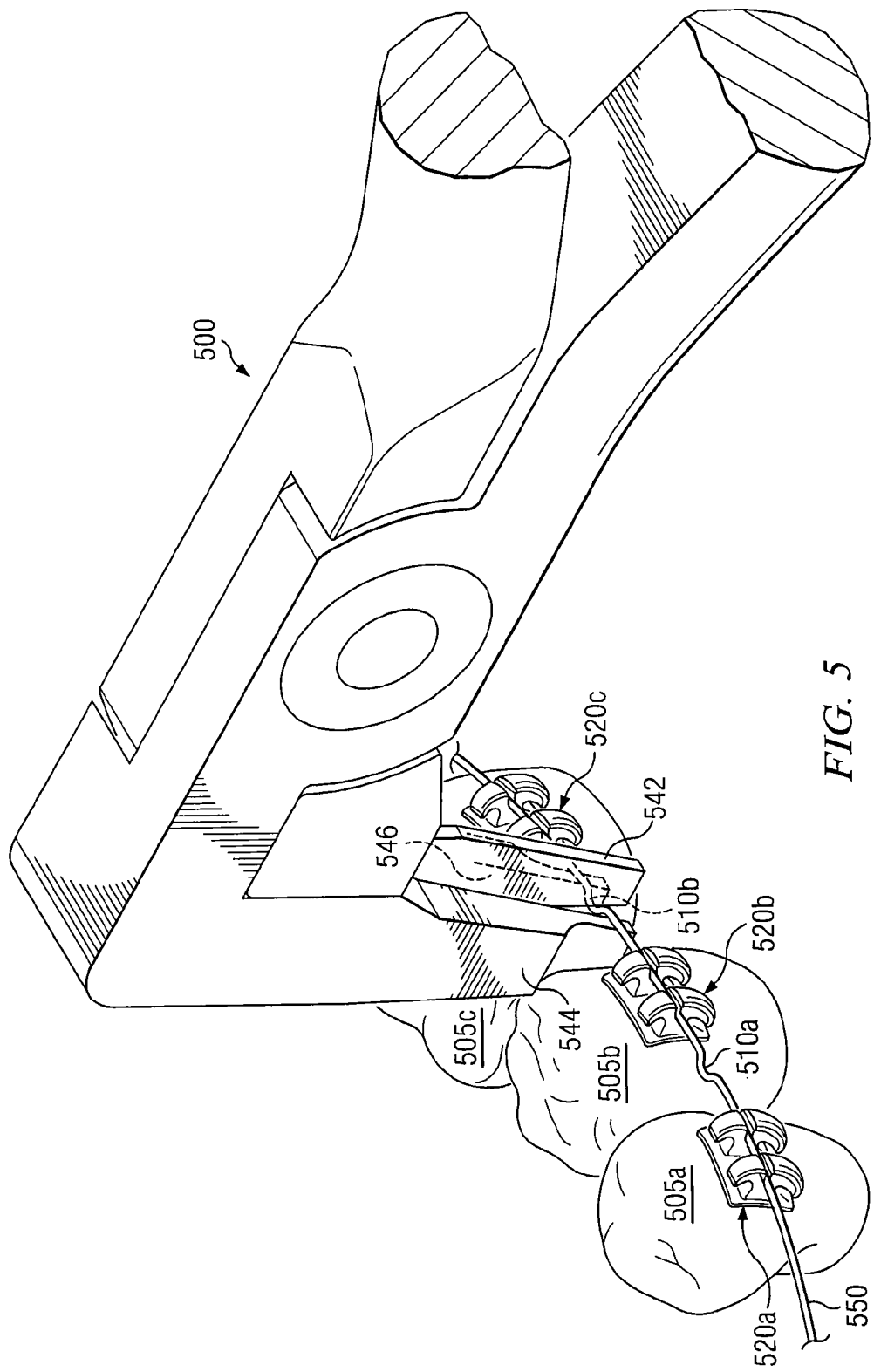
FIG. 5 illustrates example wire adjustments that may be made to an orthodontic arch wire using a handheld apparatus according to an alternative embodiment.

FIG. 5 illustrates example adjustments that may be made to an orthodontic arch wire 550 using another example embodiment of a handheld apparatus 500. As shown in FIG. 5, handheld apparatus 500 may be manipulated so as to form inward-directional bends 510a and 510b in an orthodontic arch wire 550. The three prongs 542, 544 and 546 of handheld apparatus 500 may be shaped in a manner that enables their manipulation between brackets 520a, 520b, and/or 520c. Thus, particular embodiments of handheld apparatus 500 may be used to make controlled "first order" (inward and/or outward) intra-oral adjustments of orthodontic arch wire 550 at a location between two closely spaced brackets 520a and 520b coupled to teeth 505a and 505b, respectively. Handheld apparatus 500 may also be used to bend arch wires outside of a patient's mouth and may be used to make a variety of alternative bends oriented in alternative directions.

Particular embodiments may provide a number of technical advantages. In certain embodiments, a multi-pronged handheld apparatus may have prong tips shaped for particular applications. For example, some embodiments may enable intra-oral adjustments of an arch wire within a patent's mouth. The prongs of some embodiments may each have respective tips that may be manipulated within limited spaces, such as, for example, between dental braces and/or between the arch wire and the patient's teeth. In addition, the prong tips may be configured to facilitate controlled, consistent, and/or delicate wire adjustments. The prong tips of various embodiments may be shaped in a manner that mitigates the risk of nicking or fracturing the arch wire during an adjustment. In particular embodiments, some embodiments may have prong tips that are narrowed with respect to a broader prong base, thereby facilitating particular arch wire adjustments while enhancing structural rigidity of the prongs.

Although the present invention has been described above in connection with several embodiments, a myriad of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A handheld apparatus for adjusting orthodontic wire, comprising:
  a first handle portion pivotably coupled to a second handle portion such that the first and second handle portions are capable of pivoting with respect to each other at a pivot axis; and
  a jaw portion extending from the first and second handle portions, the jaw portion comprising:
    a first prong extending from the first handle portion; and
    second and third prongs extending from the second handle portion, the second and third prongs separated from each other by a slot, the second and third prongs each comprising:
      an inner surface that partially defines the slot, the inner surface disposed substantially along a plane perpendicular to the pivot axis; and
      first and second outer surfaces joined together by a transition region, the first outer surface closer than the second outer surface to the plane of the inner surface perpendicular to the pivot axis, the second outer surface closer than the first outer surface to the pivot axis, the first and second outer surfaces disposed opposite from the inner surface; and
  wherein the first and second handle portions are further configured to pivot with respect to each other at the pivot axis such that the first prong opposes the slot separating the second and third prongs;
  wherein the maximum distance between the first outer surfaces of the second and third prongs along a line parallel to the pivot axis is less than or equal to 6 mm; and
  wherein the minimum distance between the second outer surface of the second and third prongs along a line parallel to the pivot axis is greater than or equal to 4 mm.

2. The handheld apparatus of claim 1, wherein the jaw portion extends from the first and second handle portions at approximately a ninety-degree angle relative to a plane parallel and through the pivot axis, the plane parallel and through the pivot axis being between the first and second handle portions and being substantially equidistant from the first and second handle portions.

3. The handheld apparatus of claim 2, wherein the first prong of the jaw portion that extends from the first and second handle portions at approximately a ninety-degree angle relative to a plane parallel and through the pivot axis is further from the pivot axis than the second and third prongs of the jaw portion that extends from the first and second handle portions at approximately a ninety-degree angle relative to a plane parallel and through the pivot axis.

4. The handheld apparatus of claim 2, wherein the first prong of the jaw portion that extends from the first and second handle portions at approximately a ninety-degree angle relative to a plane parallel and through the pivot axis is closer to the pivot axis than the second and third prongs of the jaw portion that extends from the first and second handle portions at approximately a ninety-degree angle relative to a plane parallel and through the pivot axis.

5. The handheld apparatus of claim 1, wherein a second plane parallel and through the pivot axis and substantially equidistant from the first and second handle portions is between the first prong and the second and third prongs and is substantially equidistant from the first prong and the second and third prongs.

6. The handheld apparatus of claim 1, wherein the inner surface of the second prong is substantially parallel to the inner surface of the third prong.

7. The handheld apparatus of claim 1, wherein the first outer surface of the second prong is substantially planar and parallel to the first outer surface of the third prong.

8. The handheld apparatus of claim 1, wherein the first outer surface of the second prong is joined to the inner surface of the second prong by one or more chamfered edges capable of distributing pressure applied to the surface of an orthodontic wire by the jaw portion.

9. The handheld apparatus of claim 1, wherein the first handle portion and the first prong each form respective portions of a single metallic piece.

10. The handheld apparatus of claim 1, wherein the transition region of the second prong is selected from the group consisting of:
a rounded fillet;
a step;
a tapered step; and
an S-curve.

11. A handheld apparatus for adjusting orthodontic wire, comprising:
a first handle portion pivotably coupled to a second handle portion such that the first and second handle portions are capable of pivoting with respect to each other at a pivot axis; and
a jaw portion extending from the first and second handle portions, the jaw portion comprising:
a first prong extending from the first handle portion; and
second and third prongs extending from the second handle portion, the second and third prongs separated from each other by a slot, and the second and third prongs each comprising:
a substantially rectangular cross-section at a right angle to an inner surface that partially defines the slot, the inner surface disposed substantially along a first plane perpendicular to the pivot axis; and
first and second outer surfaces joined together by a fillet, the first outer surface closer than the second outer surface to the plane of the inner surface perpendicular to the pivot axis, the second outer surface closer than the first outer surface to the pivot axis, and the first and second outer surfaces disposed opposite from the inner surface; and
wherein a second plane parallel and through the pivot axis and substantially equidistant from the first and second handle portions is between the first prong and the second and third prongs and is substantially equidistant from the first prong and the second and third prongs;
wherein the first outer surface of the second prong is joined to the inner surface of the second prong by one or more chamfered edges capable of distributing pressure applied to the surface of an orthodontic wire by the jaw portion;
wherein the inner surface of the second prong is substantially parallel to the inner surface of the third prong;
wherein the first outer surface of the second prong is substantially planar and parallel to the first outer surface of the third prong;
wherein the first handle portion and the first prong each form respective portions of a single metallic piece;
wherein the first and second handle portions are further configured to pivot with respect to each other at the pivot axis such that the first prong opposes the slot separating the second and third prongs;
wherein the maximum distance between the first outer surfaces of the second and third prongs along a line parallel to the pivot axis is less than or equal to 6 mm; and
wherein the minimum distance between the second outer surface of the second and third prongs along a line parallel to the pivot axis is greater than or equal to 4 mm.

12. A handheld apparatus for adjusting orthodontic wire, comprising:
a first handle portion pivotably coupled to a second handle portion such that the first and second handle portions are capable of pivoting with respect to each other at a pivot axis; and
a jaw portion extending from the first and second handle portions at approximately a ninety-degree angle relative to a plane parallel and through the pivot axis, the plane parallel and through the pivot axis being between the first and second handle portions and being substantially equidistant from the first and second handle portions, the jaw portion comprising:
a first prong extending from the first handle portion; and
second and third prongs extending from the second handle portion, the second and third prongs separated from each other by a slot, and the second and third prongs each comprising:
a substantially rectangular cross-section;
an inner surface that partially defines the slot, the inner surface disposed substantially along a plane perpendicular to the pivot axis; and
first and second outer surfaces joined together by a fillet, the first outer surface closer than the second outer surface to the plane of the inner surface perpendicular to the pivot axis, the second outer surface closer than the first outer surface to the pivot axis, and the first and second outer surfaces disposed opposite from the inner surface along respective axes that are each parallel to the pivot axis; and
wherein the first outer surface of the second prong is joined to the inner surface of the second prong by one or more chamfered edges capable of distributing pressure applied to the surface of an orthodontic wire by the jaw portion;
wherein the inner surface of the second prong is substantially parallel to the inner surface of the third prong;
wherein the first outer surface of the second prong is substantially planar and parallel to the first outer surface of the third prong;
wherein the first handle portion and the first prong each form respective portions of a single metallic piece;
wherein the first and second handle portions are further configured to pivot with respect to each other at the pivot axis such that the first prong opposes the slot separating the second and third prongs;
wherein the maximum distance between the first outer surfaces of the second and third prongs along a line parallel to the pivot axis is less than or equal to 6 mm; and wherein the minimum distance between the second outer surface of the second and third prongs along a line parallel to the pivot axis is greater than or equal to 4 mm.

13. The handheld apparatus of claim 12, wherein the first prong of the jaw portion that extends from the first and second handle portions at approximately a ninety-degree angle relative to a plane parallel and through the pivot axis is further from the pivot axis than the second and third prongs of the jaw portion that extends from the first and second handle portions at approximately a ninety-degree angle relative to a plane parallel and through the pivot axis.

14. The handheld apparatus of claim 12, wherein the first prong of the jaw portion that extends from the first and second handle portions at approximately a ninety-degree angle relative to a plane parallel and through the pivot axis is closer to the pivot axis than the second and third prongs of the jaw portion that extends from the first and second handle portions at approximately a ninety-degree angle relative to a plane parallel and through the pivot axis.

* * * * *